United States Patent [19]

Platzek et al.

[11] Patent Number: 6,080,785
[45] Date of Patent: Jun. 27, 2000

[54] MONOFUNCTIONALISED EDTA, DTPA AND TTHA DERIVATIVES AND THEIR USE IN MEDICAL DIAGNOSIS AND THERAPY

[75] Inventors: Johannes Platzek; Peter Mareski; Ulrich Niedballa; Bernd Radüchel, all of Berlin, Germany

[73] Assignee: Schering Aktiengesellschaft, Berlin, Germany

[21] Appl. No.: 09/101,032

[22] PCT Filed: Dec. 20, 1996

[86] PCT No.: PCT/DE96/02476

§ 371 Date: Jun. 29, 1998

§ 102(e) Date: Jun. 29, 1998

[87] PCT Pub. No.: WO97/25305

PCT Pub. Date: Jul. 17, 1997

[30] Foreign Application Priority Data

Jan. 4, 1996 [DE] Germany ............................ 196 01 060

[51] Int. Cl.$^7$ .......................... A01N 37/02; A01N 37/08; C07C 69/74; C07C 229/24
[52] U.S. Cl. .......................... 514/547; 514/530; 560/121; 560/169
[58] Field of Search ..................................... 560/121, 169; 514/530, 547

[56] References Cited

U.S. PATENT DOCUMENTS

| | | | |
|---|---|---|---|
| 5,514,810 | 5/1996 | Platzek et al. | 548/300.1 |
| 5,618,513 | 4/1997 | Srinivasan | 424/1.69 |

FOREIGN PATENT DOCUMENTS

| | | |
|---|---|---|
| 0 331 616 | 9/1989 | European Pat. Off. . |
| 1 076 146 | 7/1967 | United Kingdom . |
| 1 453 694 | 10/1996 | United Kingdom . |

OTHER PUBLICATIONS

Journal of Medicinal Chemistry, Aug. 30, 1996.

*Primary Examiner*—Gary Geist
*Assistant Examiner*—Brian J. Davis
*Attorney, Agent, or Firm*—Millen, White, Zelano & Branigan, P.C.

[57] ABSTRACT

The invention relates to new monofunctionalized ethylenediaminetetraacetic acid, diethylenetriaminepentaacetic acid and triethylenetetraaminehexaacetic acid derivatives, their production and their use for the production of pharmaceutical agents.

17 Claims, No Drawings

MONOFUNCTIONALISED EDTA, DTPA AND TTHA DERIVATIVES AND THEIR USE IN MEDICAL DIAGNOSIS AND THERAPY

FIELD OF INVENTION

The invention relates to new monofunctionalized EDTA, DTPA and TTHA derivatives and their use for the production of pharmaceutical agents.

Metal complexes that consist of an open-chain chelating agent (ligands) and metal ions are known pharmaceutical agents, which have a variety of uses in medical diagnosis and therapy of heavy metal poisoning. Thus, i.a., the meglumine salt of the gadolinium(III) complex of diethylenetriaminepentaacetic acid (DTPA) was approved under the trade name Magnevist® as a contrast medium for MR tomography.

For the development of new preparations, it is often necessary to bond one or more ligands that are capable of chelation, such as, e.g, ethylenediaminetetraacetic acid (EDTA), diethylenetriaminepentaacetic acid (DTPA) or triethylenetetraaminehexaacetic acid (TTHA) to another molecule. Thus, it is possible, e.g., to bond a DTPA radical to a monoclonal antibody, which for its part has a specificity relative to tumors in order to label and thus to detect the latter, using a complexed radioactive metal ion. Such a process was described by, e.g., Kuhlmann and Steinstrasser (Nucl. Med. Biol. 15 (1988), pp. 617–627). In addition, it is possible to bond several complexing agent radicals to a polymeric parent substance and thus to increase the number of metal ions, which are present as opacifying components in the molecule. Compounds of this type are described in, for example, European Patent Application EP 331616.

For the production of such compounds, appropriately prepared monofunctionalized complexing agent derivatives are always required. Thus, e.g., Kuhlmann and Steinstrasser use the bis-anhydride of DTPA (Int. J. Radiat. Isot. 33 (1982), pp. 327–332) that is described for the first time by Hnatowich. The main problem when using bis-anhydride of DTPA is, however, its poor solubility in organic solvents, which entails a host of other problems.

Another problem of use of the bis-anhydride of DTPA for linking DTPA to amine-containing molecules is the unavoidable crosslinking, as was documented by a critical study by Maisano et al. (Bioconj. Chem. 3 (1992), pp. 212–217). For this reason, the inventors of European Patent Application EP 331616 propose the use of a monoanhydride, which also carries an ethyl ester (see Example 13a), that is obtained from the bis-anhydride. This derivative shows a better, but still always unsatisfactory solubility and at the same time exhibits a radical with the ethyl ester group that is easy to saponify unintentionally and is therefore difficult to handle. Moreover, the synthesis is expensive, i.a., because of the necessary chromatographic separations.

The partial alkaline saponification of DTPA-pentamethyl ester, as it is described in U.S. Pat. No. 5,252,317, invariably leads to product mixtures, since saponification by nature proceeds statistically.

SUMMARY OF THE INVENTION

The object of this invention was therefore to make available new derivatives of EDTA, DTPA and TTHA, which make possible selective coupling to additional molecules. They are also to be easy to manufacture and to have better solubility than the known derivatives. At the same time, they are to carry carboxylic acid protective groups, which if desired can be readily and selectively cleaved, but which are not unintentionally cleaved during the course of further manipulations of the molecule.

This object is achieved by this invention, especially by the new materials and the production process of this invention. Advantageous embodiments of the invention are also disclosed.

The subjects of this invention are therefore compounds of general formula I

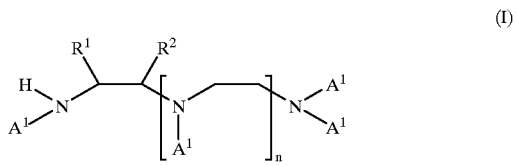

in which n stands for numerical values 0, 1 or 2, $A^1$ stands for radical —$CH_2CO_2{}^tBu$, $R^1$ and $R^2$ either in each case stand for hydrogen or together stand for —$(CH_2)_m$—, in which m can assume numerical values 3 to 6, provided that $R^1$ and $R^2$ only then together stand for —$(CH_2)_m$—, if n stands for value 0.

Formula I relates to EDTA-(n=0), DTPA-(n=1) and TTHA-(n=2) derivatives, in which in each case a terminal acetic group is substituted by hidrogen but preferably DTPA derivatives. The acetic acid functions in groups $A^1$ are laid out in the form of their tert-butyl esters. The latter have the advantage that if desired they can be readily and selectively cleaved by treatment with trifluoroacetic acid. The compounds are readily soluble in organic solvents, so that they can be linked at one site to a considerable number of molecules. After the acid protective groups are cleaved off, then metal complexes can be formed, which are suitable for medical application in diagnosis and/or therapy.

The invention further relates to compounds of general formula II

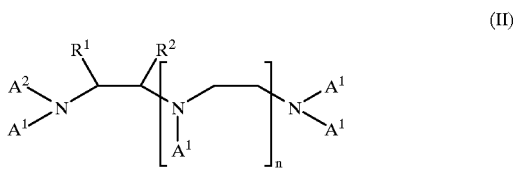

in which n stands for numerical values 0, 1 or 2, $A^1$ stands for radical —$CH_2CO_2{}^tBu$, $A^2$ stands for radical —$CH_2CO_2H$, $R^1$ and $R^2$ either in each case stand for hydrogen or together stand for —$(CH_2)_m$—, in which m can assume numerical values 3 to 6, provided that $R^1$ and $R^2$ only then together stand for —$(CH_2)_m$—, if n stands for value 0.

The compounds of general formula II also relate to EDTA, DTPA and TTHA derivatives. Of the acetic acid groups that are present in the compounds, one is present as a free acid group; the radical is in turn designed as a tert-butyl ester. These compounds also exhibit excellent solubility in organic solvents, so that similar to the compounds of general formula I, they can be linked at one site and securely to a considerable number of molecules. In the case of EDTA derivatives, groups $R^1$ and $R^2$ together can also stand for an oligomethylene radical, so that together with the two carbon atoms of the backbone, a cycloalkyl ring, preferably a cyclohexyl ring, is produced.

The invention further relates to a process for the production of the compounds of general formula I

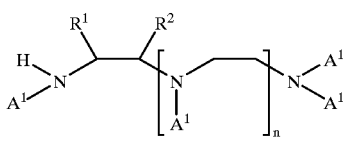

(I)

in which n stands for numerical values 0, 1 or 2, $A^1$ stands for radical —$CH_2CO_2{}^tBu$, $R^1$ and $R^2$ either in each case stand for hydrogen or together stand for —$(CH_2)_m$—, in which m can assume numerical values 3 to 6, provided that $R^1$ and $R^2$ only then together stand for —$(CH_2)_m$—, if n stands for value 0.

characterized in that a compound of general formula III

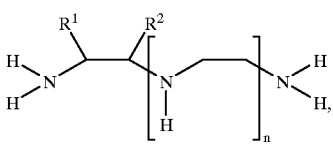

(III)

in which $R^1$, $R^2$ and n have the above-mentioned meanings, is reacted with a protective group reagent to a compound of general formula IV

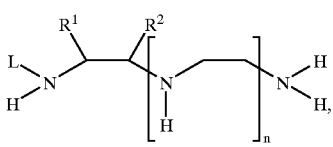

(IV)

in which $R^1$, $R^2$ and n have the above-mentioned meanings, and L stands for a trifluoroacetyl group or a benzyl group, the latter is reacted with compounds of general formula V

 (V)

in which X stands for chlorine, bromine or iodine, and the thus obtained compound is converted into the compound of general formula I by cleaving protective group L.

The introduction of protective groups L takes place in such a way that either the trifluoroacetyl protective group is introduced in that the amine that is used as educt is reacted with trifluoroacetic acid ethyl ester, or that the benzyl protective group is introduced in such a way that first the amine is reacted with benzaldehyde, and the resulting product is reduced with sodium borohydride. The intermediate product of general formula IV that is thus produced in any case is then reacted with haloacetic acid tert-butyl ester. After protective group L is cleaved off by alcoholic ammonolysis of the trifluoroacetyl group or by catalytic hydrogenation of the benzyl group, the desired compound of general formula I is obtained directly. Detailed conditions and procedures are disclosed in the examples. One skilled in the art has the necessary technical knowledge to modify the syntheses and thus to match them to their respective needs.

The subject of the invention is also a process for the production of the compounds of general formula II, which is characterized in that the compound of general formula I is reacted with haloacetic acid (chloro-, bromo- or iodoacetic acid). This process can also be designed in such a way that the reaction is done with a haloacetic acid ester, whereby as an ester group a group is selected that can be saponified without influencing the tert-butyl ester groups. It is possible, for example, to react a compound of general formula I with haloacetic acid benzyl ester. The benzyl radical can be removed by catalytic hydrogenation (catalyst, e.g., palladium on activated carbon) from the compound that is produced, whereby the compound of general formula II is obtained. Analogously to this variant, a reaction of a compound of general formula I with haloacetic acid methyl ester and the subsequent cleavage of the methyl radical with an equivalent quantity of base can also be done.

The compounds of general formulas I and II can be used in a variety of ways for the production of agents for medical diagnosis or therapy. They are used especially for the production of agents for MRI diagnosis, for diagnostic radiology or for radiodiagnosis. They are also used, however, for the production of agents for radiotherapy. Details of the types of use mentioned above can be deduced from, e.g., EP 430863.

The compounds can also be used for the production of agents that act as antidotes in the case of heavy metal poisoning.

The invention therefore also relates to the above-mentioned uses for the production of pharmaceutical agents.

The examples below are to describe the subject of the invention without intending that it be limited to these examples:

EXAMPLE 1

6,9-Bis(t-butoxycarbonylmethyl)-3-carboxymethyl-3,6,9-triazaundecanedicarboxylic acid-di-t-butyl ester a) 1-Trifluoroacetyl-1,4,7-triazaheptane 21.6 ml (200 mmol) of 1,4,7-triazaheptane is dissolved in 300 ml of absolute tetrahydrofuran under covering with nitrogen. It is cooled to 0° C., and then 26.2 ml (220 mmol) of trifluoroacetic acid ethyl ester in 400 ml of absolute tetrahydrofuran is dissolved in it. After stirring overnight at room temperature, it is concentrated by evaporation in a vacuum at a bath temperature of 35–40° C.

Yield: 39.6 g (99.4% of theory)

After thin-layer chromatography (silica gel, dioxane/water/ammonia=10/1/1), the reaction product consists of a mixture of monoamide and diamide at a ratio of 9:1.

Elementary analysis: $C_6H_{12}F_3N_3O$

| | | | | |
|---|---|---|---|---|
| Cld: | C 36.18 | H 6.07 | F 28.62 | N 21.10 |
| Fnd: | C 35.51 | H 5.57 | F 30.65 | N 19.78 | b) 6,9-Bis(t-butyloxycarbonylmethyl)-3-trifluoroacetyl-3,6,9-triaza-undecanedicarboxylic acid-di-t-butyl ester 39.6 g (178.9 mmol of monoamide) of the amide mixture that is produced under 1a) is dissolved in 450 ml of absolute dimethylformamide. It is mixed with 138.21 g (1000 mmol) of powdered potassium carbonate, then 195.06 g (1 mol) of bromoacetic acid-t-butyl ester is added in drops to it while being cooled with ice, and the reaction is completed by stirring overnight at room temperature. It is diluted with diethyl ether, salts are suctioned out, the filtrate is concentrated by evaporation in a vacuum, and then the dimethylformamide is drawn off in an oil pump vacuum. The residue is purified by column chromatography on silica gel. A mixture of hexane and ethyl acetate is used as an eluant.

Yield: 104.1 g (88.7% of theory)

Elementary analysis: $C_{30}H_{52}F_3N_3O_9$

| Cld: | C 54.95 | H 7.99 | F 8.69 | N 6.41 |
| --- | --- | --- | --- | --- |
| Fnd: | C 54.99 | H 8.06 | F 8.64 | N 6.39 | c) 6,9-Bis(t-butoxycarbonylmethyl)-3,6,9-triazaundecanedicarboxylic acid-di-t-butyl ester 32.79 g (50 mmol) of the compound that is produced under 1b) is dissolved in 400 ml of methanol. It is mixed with 200 ml of concentrated ammonia and allowed to stir over the weekend at room temperature. The thin-layer chromatogram shows that no more starting compound is present. It is concentrated by evaporation in a vacuum, taken up in dichloromethane, washed with water, the organic solution is dried on sodium sulfate and evaporated to the dry state in a vacuum. The title compound is obtained as a viscous oil.

Yield: 26.64 g (95.2% of theory)

Elementary analysis: $C_{28}H_{53}N_3O_8$

| Cld: | C 60.06 | H 9.54 | N 7.54 |
| --- | --- | --- | --- |
| Fnd: | C 60.11 | H 9.60 | N 7.49 | d) 3-Benzyloxycarbonylmethyl-6,9-bis(t-butoxycarbonylmethyl)-3,6,9-triazaundecanedicarboxylic acid-di-t-butyl ester 14.0 g (25 mmol) of the compound that is produced under 1c) is dissolved in 120 ml of absolute dimethylformamide. It is mixed with 3.86 g (28 mmol) of powdered potassium carbonate, cooled to 0° C., and then 5.96 g (26 mmol) of bromoacetic acid benzyl ester is added in drops to it. It is allowed to stir overnight at room temperature, poured onto ice water, taken up in ethyl acetate, the organic solution is dried on sodium sulfate and evaporated to the dry state in a vacuum. The title compound is purified by column chromatography on silica gel. A mixture of hexane and ethyl acetate is used as an eluant. The title compound is a viscous oil.

Yield: 15.47 g (87.4% of theory)

Elementary analysis: $C_{37}H_{61}N_3O_{10}$

| Cld: | C 62.76 | H 8.68 | N 5.96 |
| --- | --- | --- | --- |
| Fnd: | C 62.81 | H 8.73 | N 5.99 | e) 6,9-Bis(t-butoxycarbonylmethyl)-3-carboxymethyl-3,6,9-triazaundecanedicarboxylic acid-di-t-butyl ester 7.08 g (10 mmol) of the compound that is produced under 1d) is dissolved in 200 ml of isopropanol. It is mixed with 250 mg of catalyst (Pd 20%C), evacuated, aerated with hydrogen and hydrogenated at normal pressure. 224 ml of hydrogen is taken up. Catalyst is filtered out, rewashed well with isopropanol, and the solution is evaporated to the dry state in a vacuum. The title compound is obtained as a foam.

Yield: 5.91 g (95.6% of theory)

Elementary analysis: $C_{30}H_{55}N_3O_{10}$

| Cld: | C 58.33 | H 8.97 | N 6.80 |
| --- | --- | --- | --- |
| Fnd: | C 58.30 | H 9.00 | N 6.75 | f) 6,9-Bis(tert-butoxycarbonylmethyl)-3-pentylaminocarbonylmethyl-3,6,9-triazaundecanedioic acid-di-tert-butyl-ester 5.00 g (7.91 mmol) of the title compound of Example 1e) is dissolved in 25 ml of dimethylformamide, and 894 mg (7.77 mol) of N-hydroxysuccinimide is added. It is cooled to 0° C., and 1.603 g (7.77 mmol) of dicyclohexylcarbodiimide is added. It is stirred for one hour at 0° C. and then for 4 hours at room temperature. It is cooled to 0° C., and a solution of 0.62 g of pentylamine (7.06 mmol) in 10 ml of dimethylformamide is added in drops within 10 minutes. It is stirred for one hour at 0° C., then overnight at room temperature. After the solvent is drawn off in a vacuum, it is evaporated to the dry state, and the residue is taken up in 100 ml of ethyl acetate. Precipitated urea is filtered out, and the filtrate is washed twice with 100 ml of 5% aqueous soda solution each. The organic phase is dried on magnesium sulfate and evaporated to the dry state in a vacuum. The residue is chromatographed on silica gel (mobile solvent: n-hexane/ethyl acetate 20:1). 4.81 g of the title compound (88% of theory) is obtained as a colorless oil.

Elementary analysis:

| Cld: | C 64.92 | H 9.34 | N 7.21 |
| --- | --- | --- | --- |
| Fnd: | C 64.81 | H 9.28 | N 7.25 | g) 6,9-Bis-(carboxymethyl)-3-pentylaminocarbonylmethyl-3,6,9-triazaundecanedioic acid 4.50 g (5.79 mmol) of the title compound of Example 1f) is dissolved in 100 ml of trifluoroacetic acid. It is stirred overnight at room temperature. It is evaporated to the dry state in a vacuum, and the residue is chromatographed on silica gel (mobile solvent: ethanol/25% aqueous ammonia solution 20:1). The fractions that contain the product are evaporated to the dry state in a vacuum. The residue is dissolved in 100 ml of water. 20 ml of acidic ion exchanger IR 120 (H+-form) is added and stirred for 10 minutes at room temperature. Ion exchanger is filtered out and evaporated to the dry state in a vacuum.

Yield: 2.35 g (69% of theory) of a vitreous solid Water content: 3.44%

Elementary analysis (relative to anhydrous substance):

| Cld: | C 56.51 | H 7.30 | N 10.14 |
| --- | --- | --- | --- |
| Fnd: | C 56.61 | H 7.22 | N 10.03 | h) Gadolinium complex of 6,9-bis(carboxymethyl)-3-pentyl-aminocarbonylmethyl-3,6,9-triazaundecanedioic acid-mono-sodium salt 2.5 g (4.52 mmol) of the title compound of Example 1g) is dissolved in 75 ml of distilled water and mixed at room temperature in portions with a total of 1.65 g (4.57 mmol) of gadolinium oxide. After a reaction time of 3 hours at 80° C., the now clear reaction solution is cooled to room temperature, and a pH of 7.2 is set. After filtration with PTFE filters, the filtrate that is thus obtained is freeze-dried.

Yield: g.48 (69% of theory) of an amorphous powder
Water content: 3.59%
Elementary analysis (relative to anhydrous substance):

| Cld: | C 41.54 | H 5.86 | N 7.75 | Gd 21.75 | Na 3.18 |
|---|---|---|---|---|---|
| Fnd: | C 41.62 | H 5.91 | N 7.71 | Gd 21.92 | Na 3.25 |

EXAMPLE 2
6,9-Bis(t-butoxycarbonylmethyl)-3-carboxymethyl-3,6,9-triazaundecanedicarboxylic acid-di-t-butyl ester a) 1-Benzyl-1,4,7-triazaheptane A stirred solution of 108.26 ml (998 mmol) of 1,4,7-triaza-heptane in 750 absolute methanol is mixed at 0° C. drop by drop with a solution of 20.0 g (188 mmol) of benzaldehyde in 100 ml of absolute methanol. After a reaction time of 2 hours at 0° C., it is mixed in portions with a total of 7.13 g (188 mmol) of sodium borohydride and stirred for another 12 hours at 25° C. For working-up, the reaction mixture is filtered on diatomaceous earth, and the solvent is drawn off in a vacuum. The remaining oily residue is mixed with dichloromethane (250 ml) and water (250 ml) and extracted. After extraction of the aqueous phase is again performed with dichloromethane, the combined organic phases are dried on sodium sulfate, filtered, and the solvent is drawn off in a vacuum. The residue is chromatographed on silica gel (eluant: methanol/aqueous ammonia solution 20/1).

Yield: 31.52 g (86.7% of theory) of a colorless oil
Elementary analysis: $C_{11}H_{19}N_3$

| Cld: | C 68.35 | H 9.91 | N 21.74 |
|---|---|---|---|
| Fnd: | C 67.96 | H 9.88 | N 21.70 | b) 6,9-Bis(t-butyloxycarbonylmethyl)-3-benzyl-3,6,9-triaza-undecanedicarboxylic acid-di-t-butyl ester 19.54 g (101.1 mmol) of the title compound that is produced under 2a) is dissolved in a mixture of 400 ml of tetrahydrofuran and 80 ml of water and mixed with 64.3 g (465.15 mmol) of potassium carbonate. Then, 90.75 g (465.15 mmol) of bromoacetic acid-t-butyl ester is added in drops, and the reaction solution is refluxed for 3 hours. After cooling to room temperature, the aqueous phase is separated and extracted once more with 200 ml of ethyl acetate. The combined organic phases are washed once with saturated sodium chloride solution and dried on sodium sulfate. It is filtered, and the solvent is completely drawn off in a vacuum. The remaining oil is purified by column chromatography (eluant: hexane/ethyl acetate 1:1).

Yield: 48.8 g (74.4% of theory)
Elementary analysis: $C_{35}H_{59}N_3O_8$

| Cld: | C 64.69 | H 9.15 | N 6.47 |
|---|---|---|---|
| Fnd: | C 65.10 | H 9.21 | N 6.50 | c) 6,9-Bis(t-butoxycarbonylmethyl)-3,6,9-triazaundecanedicarboxylic acid-di-t-butyl ester 12.55 g (19.31 mmol) of the compound that is produced under 2b) is dissolved in 150 ml of 2-propanol. It is mixed with 1.0 g of catalyst (Pd 20%/C), evacuated, aerated with hydrogen and hydrogenated at normal pressure. After a reaction time of 5 hours at 25° C., no more starting material can be detected according to thin-layer chromatography. Catalyst is filtered out, rewashed well with 2-propanol, and the solution is evaporated to the dry state in a vacuum.

Yield: 10.57 g (97.7% of theory) as a colorless and viscous oil

Elementary analysis: $C_{28}H_{53}N_3O_8$

| Cld: | C 60.06 | H 9.54 | N 7.54 |
|---|---|---|---|
| Fnd: | C 60.13 | H 9.58 | N 7.50 | d) 3-Benzyloxycarbonylmethyl-6,9-bis(t-butoxycarbonylmethyl)-3,6,9-triazaundecanedicarboxylic acid-di-t-butyl ester Analogously to Example 1d), the reaction of 10.46 g (18.69 mmol) of the title compound of Example 2c) with 2.76 g (20 mmol) of potassium carbonate and 4.77 g (20 mmol) of bromoacetic acid benzyl ester yields 11.6 g (88.2% of theory) of the title compound as a viscous oil.

Elementary analysis: $C_{37}H_{61}N_3O_{10}$

| Cld: | C 62.76 | H 8.68 | N 5.96 |
|---|---|---|---|
| Fnd: | C 62.79 | H 8.72 | N 5.60 | e) 6,9-Bis(t-butoxycarbonylmethyl)-3-carboxymethyl-3,6,9-triazaundecanedicarboxylic acid-di-t-butyl ester Analogously to Example 1e), the hydrogenolysis of 9.74 g (13.76 mmol) of the title compound of Example 2d) using 300 mg of catalyst (Pd 20%/C) yields the title compound as a colorless foam.

Yield: 8.17 g (96.2% of theory)
Elementary analysis: $C_{30}H_{55}N_3O_{10}$

| Cld: | C 58.33 | H 8.97 | N 6.80 |
|---|---|---|---|
| Fnd: | C 58.29 | H 8.99 | N 6.74 |

EXAMPLE 3
3-Carboxymethyl-6-t-butoxycarbonylmethyl-3,6-diaza-octane-dicarboxylic acid-di-t-butyl ester a) 1-Benzyl-1,4-diazabutane 60.0 g (998 mmol) of 1,4-diazabutane is dissolved in 750 ml of absolute methanol and cooled to 0° C. At this temperature, the drop-by-drop addition of 20.0 g (188 mmol) of benzaldehyde, dissolved in 100 ml of absolute methanol, is carried out. After a reaction time of 2 hours at 0° C., the addition in portions of a total of 7.13 g (188 mmol) of sodium borohydride is carried out. After 12 hours at 25° C., the reaction solution is suctioned off on diatomaceous earth, and the solvent is drawn off in a vacuum. The remaining oily residue is taken up in 500 ml of dichloromethane and washed three times with 100 ml of water in each case. After the organic phase is dried on sodium sulfate, the solvent is drawn off in a vacuum. The oily residue that is thus obtained is chromatographed on silica gel (eluant: methanol/aqueous ammonia solution 20:1).

Yield: 24.2 g (85.7% of theory)
Elementary analysis: $C_9H_{14}N_2$

| Cld: | C 71.96 | H 9.39 | N 18.65 |
| --- | --- | --- | --- |
| Fnd: | C 71.89 | H 9.37 | N 18.60 | b) 3-Benzyl-6-t-butyloxycarbonylmethyl-3,6-diazaoctanedicarboxylic acid-di-t-butyl ester 15.04 g (100.11 mmol) of the title compound that is produced under 3a) is dissolved in a mixture of 400 ml of tetrahydrofuran and 80 ml of water and mixed with 49.76 g (360 mmol) of potassium carbonate. Then, 70.22 g (360 mmol) of bromoacetic acid-t-butyl ester is added in drops, and the reaction solution is refluxed for 3 hours. After cooling to room temperature, the aqueous phase is separated and extracted once more with 200 ml of ethyl acetate. The combined organic phases are washed once with saturated sodium chloride solution and dried on sodium sulfate. It is filtered, and the solvent is completely drawn off in a vacuum. The remaining oil is purified by column chromatography (eluant: hexane/ethyl acetate 1:1).

Yield: 47.15 g (95.6% of theory) as a colorless oil
Elementary analysis: $C_{27}H_{44}N_2O_6$

| Cld: | C 65.83 | H 9.00 | N 5.69 |
| --- | --- | --- | --- |
| Fnd: | C 65.78 | H 8.97 | N 5.68 | c) 6-t-Butoxycarbonylmethyl-3,6-diazaoctanedicarboxylic acid-di-t-butyl ester 31.11 g (63.15 mmol) of the compound that is produced under 3b) is dissolved in 250 ml of 2-propanol. It is mixed with 1.0 g of catalyst (Pd 20%/C), evacuated, aerated with hydrogen and hydrogenated at normal pressure. After a reaction time of 5 hours at 25° C., no more starting material can be detected according to thin-layer chromatography. Catalyst is filtered out, rewashed well with 2-propanol, and the solution is evaporated to the dry state in a vacuum.

Yield: 20.07 g (78.95% of theory) as a colorless oil
Elementary analysis: $C_{20}H_{38}N_2O_6$

| Cld: | C 59.68 | H 9.51 | N 6.96 |
| --- | --- | --- | --- |
| Fnd: | C 59.62 | H 9.49 | N 6.97 | d) 3-Benzyloxycarbonylmethyl-6-t-butoxycarbonylmethyl-3,6-diazaoctanedicarboxylic acid-di-t-butyl ester 6.0 g (14.91 mmol) of the title compound that is produced under 3c) is dissolved in a mixture of 125 ml of tetrahydrofuran and 25 ml of water and mixed with 2.68 g (19.38 mmol) of potassium carbonate. Then, 4.44 g (19.38 mmol) of bromoacetic acid benzyl ester is added in drops, and the reaction solution is refluxed for 3 hours. After cooling to room temperature, the aqueous phase is separated and extracted once more with 200 ml of ethyl acetate. The combined organic phases are washed once with saturated sodium chloride solution and dried on sodium sulfate. It is filtered, and the solvent is completely drawn off in a vacuum. The remaining oil is purified by column chromatography. (Eluant: hexane/ethyl acetate 1:1).

Yield: 6.76 g (82.4% of theory) as a colorless oil
Elementary analysis: $C_{29}H_{46}N_2O_8$

| Cld: | C 63.25 | H 8.42 | N 5.09 |
| --- | --- | --- | --- |
| Fnd: | C 63.31 | H 8.44 | N 5.13 | e) 3-Carboxymethyl-6-t-butoxycarbonylmethyl-3,6-diazaoctane-dicarboxylic acid-di-t-butyl ester 4.8 g (8.72 mmol) of the title compound of Example 3d) is dissolved in 50 ml of 2-propanol and mixed with 150 mg of catalyst (20% Pd/C). It is evacuated, aerated with hydrogen and hydrogenated at normal pressure for 6 hours. For working-up, catalyst is filtered out and rewashed well with 2-propanol. The filtrate is concentrated by evaporation until the dry state is reached. Column-chromatographic purification of the remaining residue on silica gel (eluant: dichloromethane/2-propanol 10:1) yields the title compound as a colorless oil.

Yield: 3.4 g (85% of theory)
Elementary analysis: $C_{22}H_{40}N_2O_8$

| Cld: | C 57.37 | H 8.75 | N 6.08 |
| --- | --- | --- | --- |
| Fnd: | C 57.29 | H 8.71 | N 6.04 |

EXAMPLE 4

(±)-Trans-N, N',N'-tri-t-butoxycarbonylmethyl-N-carboxymethyl-1,2-diaminocyclohexane a) (±)-Trans-N-benzyl-1,2-diaminocyclohexane 60.0 g (525.4 mmol) of (±)-trans-1,2-diaminocyclohexane is dissolved in 750 ml of absolute methanol and cooled to 0° C. At this temperature, the drop-by-drop addition of 10.5 g (99 mmol) of benzaldehyde, dissolved in 100 ml of absolute methanol, is carried out. After a reaction time of 2 hours at 0° C., the addition in portions of a total of 3.74 g (99 mmol) of sodium borohydride is carried out. After 12 hours at 25° C., the reaction solution is suctioned off on diatomaceous earth, and the solvent is drawn off in a vacuum. The remaining oily residue is taken up in 500 ml of dichloromethane and washed three times with 100 ml of water each. After the organic phase is dried on sodium sulfate, the solvent is drawn off in a vacuum. The oily residue that is thus obtained is chromatographed on silica gel (eluant: methanol/aqueous ammonia solution 20:1).

Yield: 93.1 g (86.8% of theory)
Elementary analysis: $C_{13}H_{20}N_2$

| Cld: | C 76.42 | H 9.87 | N 13.71 |
| --- | --- | --- | --- |
| Fnd: | C 76.40 | H 9.88 | N 13.69 | b) (±)-Trans-N-benzyl-N,N',N'-tri-t-butoxycarbonylmethyl-1,2-diaminocyclohexane 80 g (391.56 mmol) of the title compound that is produced under 4a) is dissolved in a mixture of 1000 ml of tetrahydrofuran and 250 ml of water and mixed with 195 g (1409.6 mmol) of potassium carbonate. Then, 275 g (1409.6 mmol) of bromoacetic acid-t-butyl ester is added in drops, and the reaction solution is refluxed for 3 hours. After cooling to room temperature, the aqueous phase is separated and extracted once more with 600 ml of ethyl acetate. The combined organic phases are washed once with saturated sodium chloride solution and dried on sodium sulfate. It is filtered, and the solvent is completely drawn off in a vacuum. The remaining oil is purified by column chromatography (eluant: hexane/ethyl acetate 1:1).

Yield: 197.81 (92.4% of theory) as a colorless oil
Elementary analysis: $C_{31}H_{50}N_2O_6$

| Cld: | C 68.10 | H 9.22 | N 5.12 |
|---|---|---|---|
| Fnd: | C 68.07 | H 9.20 | N 5.09 | c) (±)-Trans-N,N',N'-tri-t-butoxycarbonylmethyl-1,2-diaminocyclohexane 30.0 g (54.87 mmol) of the compound that is produced under 4b) is dissolved in 250 ml of 2-propanol. It is mixed with 1.0 g of catalyst (Pd 20%/C), evacuated, aerated with hydrogen and hydrogenated at normal pressure. After a reaction time of 5 hours at 25° C., no more starting material can be detected according to thin-layer chromatography. Catalyst is filtered out, rewashed well with 2-propanol, and the solution is evaporated to the dry state in a vacuum.

Yield: 20.8 g (83.2% of theory) as a colorless oil
Elementary analysis: $C_{24}H_{44}N_2O_6$

| Cld: | C 63.13 | H 9.71 | N 6.13 |
|---|---|---|---|
| Fnd: | C 63.11 | H 9.69 | N 6.11 | d) (+)-Trans-N,N',N'-tri-t-butoxycarbonylmethyl-N-benzyloxycarbonylmethyl-1,2-diaminocyclohexane 5.0 g (10.95 mmol) of the title compound that is produced under 4c) is dissolved in a mixture of 125 ml of tetrahydrofuran and 25 ml of water and mixed with 1.96 g (14.23 mmol) of potassium carbonate. Then, 3.2 g (14.23 mmol) of bromoacetic acid benzyl ester is added in drops, and the reaction solution is refluxed for 3 hours. After cooling to room temperature, the aqueous phase is separated and extracted once more with 200 ml of ethyl acetate. The combined organic phases are washed once with saturated sodium chloride solution and dried on sodium sulfate. It is filtered, and the solvent is completely drawn off in a vacuum. The remaining oil is purified by column chromatography (eluant: hexane/ethyl acetate 1:1).

Yield: 5.52 g (83.5% of theory) as a colorless oil
Elementary analysis: $C_{33}H_{52}N_2O_8$

| Cld: | C 65.54 | H 8.67 | N 4.63 |
|---|---|---|---|
| Fnd: | C 65.49 | H 8.63 | N 4.60 | e) (±)-Trans-N,N',N'-tri-t-butoxycarbonylmethyl-N-carboxymethyl-1,2-diaminocyclohexane 4.0 g (6.60 mmol) of the title compound of Example 4d) is dissolved in 50 ml of 2-propanol and mixed with 150 mg of catalyst (20% Pd/C). It is evacuated, aerated with hydrogen and hydrogenated at normal pressure for 6 hours. For working-up, catalyst is filtered out and rewashed well with 2-propanol. The filtrate is concentrated by evaporation until the dry state is reached. Column-chromatographic purification of the remaining residue on silica gel (eluant: dichloromethane/2-propanol 10:1) yields the title compound as a colorless oil.

Yield: 3.0 g (88.2% of theory)
Elementary analysis: $C_{26}H_{46}N_2O_8$

| Cld: | C 60.68 | H 9.01 | N 5.44 |
|---|---|---|---|
| Fnd: | C 60.70 | H 9.03 | N 5.47 |

It is claimed:

1. A compound of formula I (I)

in which n is 0, 1 or 2, $A^1$ is —$CH_2CO_2$t-Bu, $R^1$ and $R^2$ either both are hydrogen or together form —$(CH_2)_m$—, in which m is 3 to 6, provided that (a) $R^1$ and $R^2$ only form —$(CH_2)_m$—, if n is 0 and (b) if n is 0, $R_1$ nd $R_2$ are not both H.

2. A compound of formula II (II)

wherein n is 0, 1 or 2

$A^1$ is —$CH_2CO_2$t-Bu, $A^2$ is —$CH_2CO_2H$, $R^1$ and $R^2$ either both are hydrogen or together form —$(CH_2)_m$—, in which m is 3 to 6, provided that $R^1$ and $R^2$ only form —$(CH_2)_m$—, if n is 0.

3. A compound according to claim 1, wherein n is 1.

4. A compound according to claim 1, wherein $R^1$ and $R^2$ each is hydrogen.

5. A compound according to claim 1, wherein $R^1$ and $R^2$ together form —$(CH_2)_4$—.

6. A process for the production of a compound of the formula I (I)

in which n is 0, 1 or 2, $A^1$ is —$CH_2CO_2$t-Bu, $R^1$ and $R^2$ either both are hydrogen or together form —$(CH_2)_m$—, in which m is 3 to 6, provided that $R^1$ and $R^2$ form —$(CH_2)_m$—, if n is 0, comprising reacting a compound of formula III

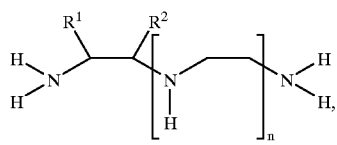

(III)

in which $R^1$, $R^2$ and n have the above-mentioned meanings, with a protective group reagent to form a compound of formula IV

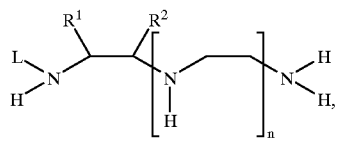

(IV)

in which $R^1$, $R^2$ and n have the above-mentioned meanings, and
L is trifluoroacetyl or benzyl,
reacting the compound of formula IV with a compound of formula V

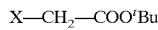    (V)

in which X is chlorine, bromine or iodine, and converting the thus obtained compound into the compound of general formula I by cleaving protective group L.

7. A compound according to claim 2, wherein n is 1.

8. A compound according to claim 2, wherein $R^1$ and $R^2$ each is hydrogen.

9. A compound according to claim 1, wherein $R^1$ and $R^2$ together form —$(CH_2)_4$—.

10. In a method of preparing a metal chelate or chelating agent from a precursor, the improvement wherein the precursor is a compound of claim 1.

11. In a method of preparing a metal chelate or chelating agent from a precursor, the improvement wherein the precursor is a compound of claim 2.

12. A method of claim 11 wherein the metal chelate is effective for MRI diagnosis, diagnostic radiology or radiodiagnosis.

13. A method of claim 11 wherein the metal chelate is effective for radiotherapy.

14. A method of claim 11 wherein the metal chelate is effective as an antidote for heavy metal poisoning.

15. A method of claim 10 wherein the metal chelate is effective for MRI diagnosis, diagnostic radiology or radiodiagnosis.

16. A method of claim 10 wherein the metal chelate is effective for radiotherapy.

17. A method of claim 10 wherein the metal chelate is effective as an antidote for heavy metal poisoning.

* * * * *